(12) United States Patent
Truwit et al.

(10) Patent No.: US 7,335,165 B2
(45) Date of Patent: Feb. 26, 2008

(54) METHOD AND APPARATUS FOR TAKING A BIOPSY

(75) Inventors: Charles L. Truwit, Wayzata, MN (US); Randal Nelson, Pine Springs, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 563 days.

(21) Appl. No.: 10/894,100

(22) Filed: Jul. 19, 2004

(65) Prior Publication Data

US 2004/0260323 A1 Dec. 23, 2004

Related U.S. Application Data

(63) Continuation of application No. 09/919,583, filed on Jul. 31, 2001, now Pat. No. 6,773,443.

(60) Provisional application No. 60/221,712, filed on Jul. 31, 2000.

(51) Int. Cl.
*A61B 17/32* (2006.01)
(52) U.S. Cl. ...................... 600/564; 606/170
(58) Field of Classification Search ............... 600/564, 600/565; 606/170, 171, 159
See application file for complete search history.

(56) References Cited

U.S. PATENT DOCUMENTS

| | | | |
|---|---|---|---|
| 3,565,062 A | 2/1971 | Kuris ........................ 606/169 |
| 4,685,458 A | 8/1987 | Leckrone ................. 128/303.1 |
| 4,886,061 A | 12/1989 | Fischell et al. ............. 128/305 |
| 5,085,662 A | 2/1992 | Willard ...................... 606/159 |
| 5,254,082 A | 10/1993 | Takase ........................ 604/22 |
| 5,527,331 A | 6/1996 | Kresch et al. .............. 606/170 |
| 5,571,130 A | 11/1996 | Simpson et al. ............ 606/171 |
| 5,662,671 A * | 9/1997 | Barbut et al. ............... 606/170 |
| 5,674,235 A | 10/1997 | Parisi ......................... 606/169 |
| 5,792,166 A | 8/1998 | Gordon et al. .............. 606/170 |
| 6,027,514 A | 2/2000 | Stine et al. ................. 606/159 |
| 6,068,603 A * | 5/2000 | Suzuki ....................... 600/565 |
| 6,120,519 A | 9/2000 | Weber et al. ............... 606/170 |
| 6,273,862 B1 | 8/2001 | Privitera et al. ............ 600/568 |

OTHER PUBLICATIONS

"Innovative Products Energy-Based Products", http://www.ethiconendo.com/ultrasonic.jsp, Ethicon Endo-Surgery, Inc. Johnson & Johnson Company,(Sep. 19, 2003),5 pages.

* cited by examiner

*Primary Examiner*—Michael Thaler
(74) *Attorney, Agent, or Firm*—Schwegman, Lundberg & Woessner, P.A.

(57) ABSTRACT

There is described method and apparatus for taking a biopsy wherein the apparatus is formed of a biocompatible cylindrical member with an outer wall and a hollow core, the cylindrical member having a longitudinal axis. An opening in the outer wall of the member is provided and a cutting device cuts tissue entering the opening as it travels along the opening. Cut tissue is treated with a coagulating agent or member so that the coagulation occurs concurrently or just after the tissue is cut wherein the coagulation occurs at a trailing edge of the opening as it travels.

3 Claims, 2 Drawing Sheets

METHOD AND APPARATUS FOR TAKING A BIOPSY

RELATED APPLICATIONS

This application is a continuation of U.S. patent application Ser. No. 09/919,583, filed on Jul. 31, 2001 now U.S. Pat. No. 6,773,443 which claims priority under 35 U.S.C. § 119(e) of U.S. Provisional Application No. 60/221,712, filed Jul. 31, 2000, which applications are incorporated herein by reference.

TECHNICAL FIELD OF THE INVENTION

The present invention relates generally to the field of medicine, and more particularly to an endoscopy biopsy device and its use in medical procedures.

BACKGROUND

Intracranial endoscopy devices include both flexible and rigid endoscopes. These devices typically have at least one channel through which a biopsy device or grabbing forcep device can be delivered. As a result, the combination of a fiberoptic endoscopic channel with a second channel for biopsy device necessitates a minimum diameter. Because of this requirement, endoscopy devices are limited in their applications. Specifically, some neurosurgeons prefer not to introduce a larger caliber device through the brain parenchyma merely to gain access to the ventricular cavity.

In addition, surgeons are occasionally reluctant to biopsy intraventricular mass lesions without direct visualization because of the risk of hemorrhage. Parenchymal lesions, by virtue of their adjacent tissue, offer some support to provide a tamponading effect against hemorrhage following biopsy. Intraventricular lesions, on the other hand, provide no such structural support as a barrier to postbiopsy hemorrhage.

SUMMARY OF THE INVENTION

As described in more detail herein below, the present invention provides method and apparatus for taking a biopsy wherein the apparatus is formed of a biocompatible cylindrical member with an outer wall and a hollow core, the cylindrical member having a longitudinal axis. An opening in the outer wall of the member is provided wherein the opening travels in the direction of the longitudinal axis of the member. A cutting device cuts tissue entering the opening as it travels along the member wherein the cutting occurs in a leading edge of the opening as it travels. Cut tissue is treated with a coagulating agent or member so that the coagulation occurs just after the tissue is cut wherein the coagulation occurs at a trailing edge of the opening as it travels. The opening can be provided with a spiral shaped member having a spiral shaped opening which rotates about the axis of the cylindrical member to provide the moving opening.

DETAILED DESCRIPTION OF THE INVENTION

Figure 1:
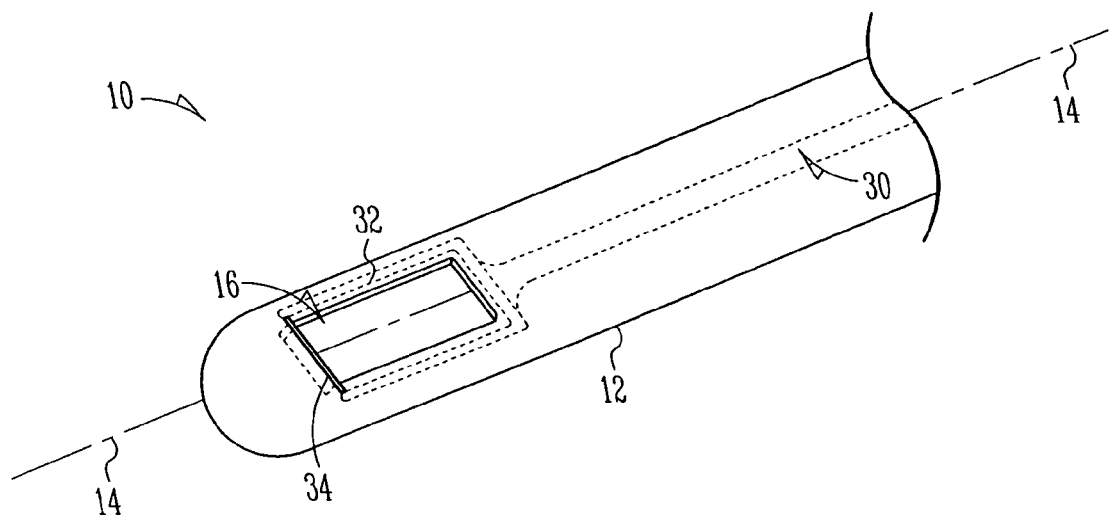
FIGS. 1-5 illustrate a biopsy device according to various example embodiments of the present invention.

In the following detailed description of the invention reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention.

Referring now to FIG. 1, there is illustrated an example embodiment of method and apparatus for taking a biopsy. An introducer 10 is formed of a biocompatible cylindrical member 12 with an outer wall and a hollow core, the cylindrical member 12 having a longitudinal axis 14. An opening 16 in the outer wall of the member is provided wherein the opening extends, in one example embodiment, in the direction of the longitudinal axis 14 of the member. A biopsy needle cutting device cuts tissue entering the opening 16 when it is positioned in a body being biopsied, for example but not by way of limitation, in a brain of a patient. In the example embodiment of FIG. 1, the biopsy needle is formed of a rod 30 with U-shaped end 32 that supports a cutting wire 34. In one embodiment, end 32 bends away from the central axis of rod 30 such that cutting wire 34 is spaced away from the axis of rod 30 with respect to a plane perpendicular to rod 30. In the case of this embodiment, the cutting wire 34 is similarly moved so as to pass under the opening 16 and cut tissue intruding into opening 16, allowing the tissue to be retrieved by extraction of the introducer 10.

Figure 3:
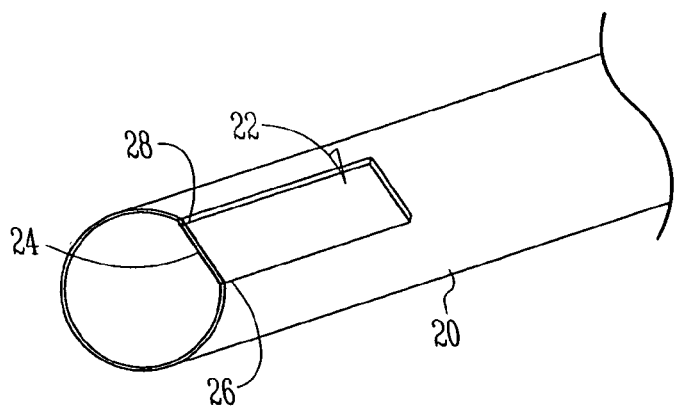

In FIG. 3, another example embodiment of a needle is formed of a hollow tube 20 having an outside diameter just smaller than the inside diameter of the introducer 10, with an opening or window 22 approximately the size of the opening 16. A cutting wire 24 is positioned on one end of the opening 22, bridging between points 26 and 28 of the end of tube 20. As tube 20 travels inside introducer 10, under control of an operator or automatic controls, with the cutting wire 24 traversing perpendicularly or at an angle to the opening 16, tissue intruding into opening 16 is cut by wire 24 and is captured in tube 20 or introducer 10, or both, either of which can be extracted from the body so that a biopsy sample can be retrieved. Tissue may be encouraged to intrude or enter into opening 16 by application of a vacuum to the introducer 10.

Figure 2:
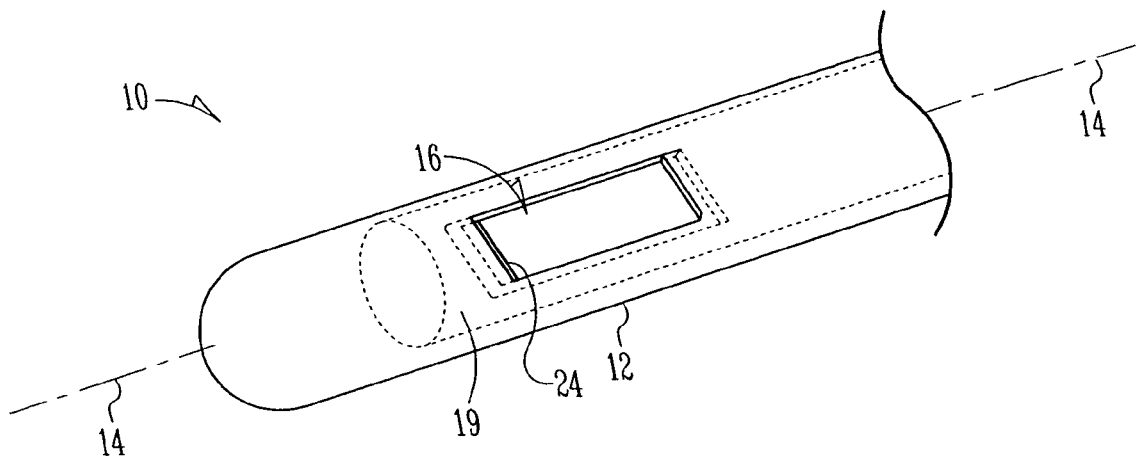

In the example embodiment of FIG. 2, the cutting needle 24 is attached on either end to the cylindrical member 12. In this embodiment, the member 12 is moved relative to a hollow tube 19 having an opening generally corresponding to opening 16, and remaining stationary while the biopsy is taken as the cutting member 24 is moved on member 12.

According to one example embodiment, the biopsy needles and introducer are made of nonconductive materials that are compatible with a magnetic resonance imaging (MRI) device. According to another sample embodiment, the cutting wires 24 and 34 are energized ultrasonically to provide for ultrasonic cutting and coagulation. The cutting wires thus first cut the sample, and then coagulate any blood or bleeding in the cut to prevent postbiopsy bleeding. In this embodiment, the wires 24 and 34 are attached on each end to respective wires that run along the biopsy needles back to an external device capable of producing the ultrasonic energy. According to yet another sample embodiment, the cutter may be formed of a wire or a formed cutting surface (for example a blade) of metal such as titanium or stainless steel or of a non-metal such as ceramic or silicon. According to yet another embodiment, the introducer 10 and biopsy needles are kept in rotational alignment using a keying system or device, so as to insure that the wire is in alignment with the biopsy window or opening 16. In addition, according to yet another embodiment, the proximal end of the needle has a mark or some other form of indication that the wire has been drawn through the length of the window. Alternatively, the cutter may be set at the proximal end of the window or opening 16 and pushed longitudinally to cut the biopsy sample. In yet another alternative embodiment, the biopsy needle is held stationary with respect to the body, and the introducer 10 is moved providing for relative movement of the cutting edge with respect to the opening 16.

According to yet another embodiment, the wires 24 and 34 may be energized at a first cutting frequency in order to traverse the opening 16 and cut the tissue therein, and then, energized at a coagulating frequency and traversed across the opening 16 a second time in order to coagulate the tissue and prevent or reduce bleeding.

Figure 4:
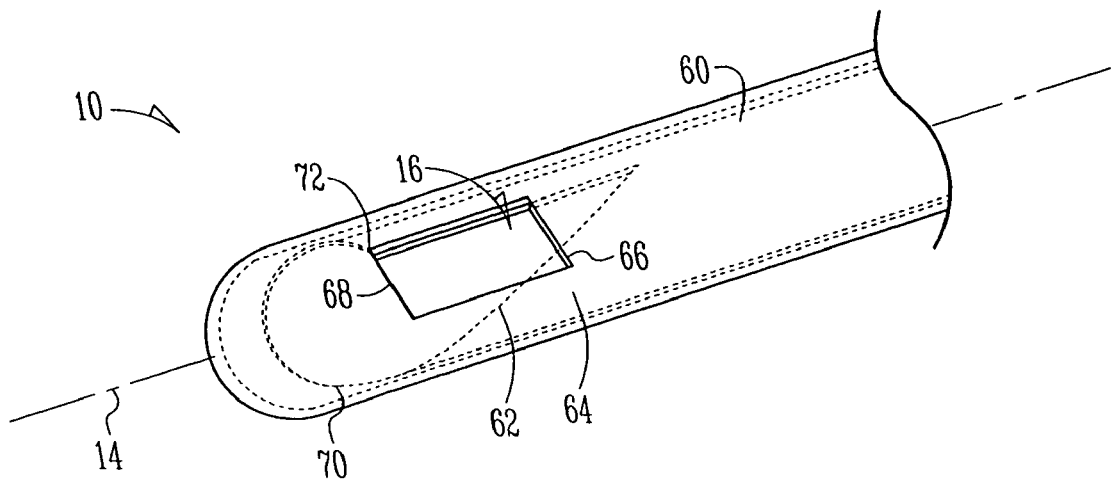

According to yet another example embodiment shown in FIG. 4, the needle 60 includes a cutting edge 62 that is formed from or along the outside circumference of the wall 64 of needle 60. This edge may be straight, or may have a crescent shape, or a combination of both, in one example embodiment. When needle 60 is rotated inside introducer 10, cutting edge 62 traverses window 16 in a direction such that the blade begins at one corner of the opening and moves diagonally across the opening to the other corner. Cutting occurs beginning at one end 66 of window 16, and continues in the direction of the end 68, until the edge 62 has completed traversing the opening 16 in its entirety such that point 70 of the cutting edge reaches point 72 at the corner of opening 16. This provides that the cutting of the tissue begins in one corner and progresses such that a greater frontal area of the tissue is cut as the blade continues to rotate. The blade thus moves in a direction that is both in part parallel to the longitudinal axis and transverse to the longitudinal axis of the introducer 10.

Figure 5:
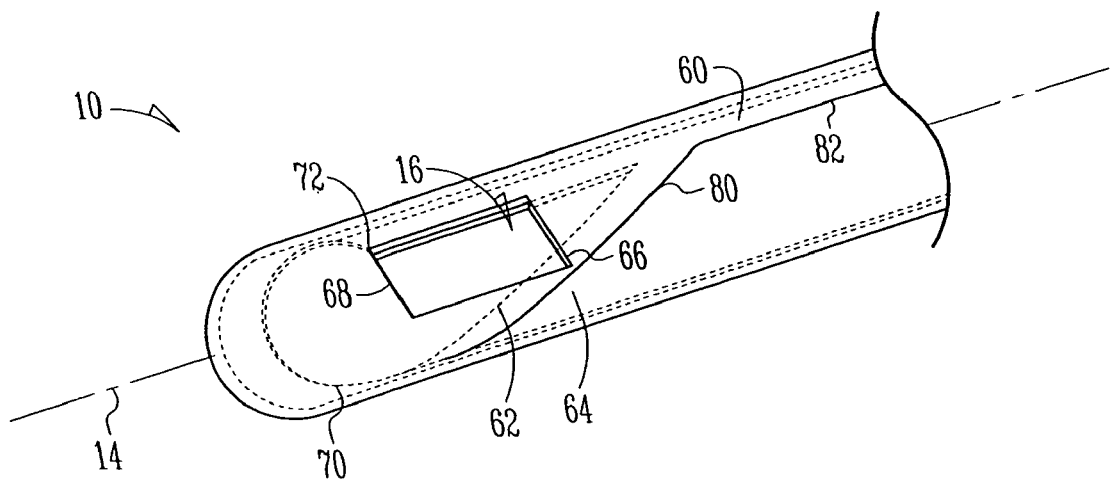

In FIG. 5, there is illustrated yet another example embodiment, identical to the embodiment of FIG. 4, except for the inclusion of a coagulating member 80 which extends along the outside of wall 64 so as to come into contact with freshly cut tissue just after cutting edge 62 has completed its cut. In this embodiment, member 80 thus prevents the cut tissue from bleeding postbiopsy. According to one embodiment, member 80 may comprise a heated wire or a coagulating agent that is, for example, impregnated in an absorbent material. In another embodiment, member 80 is the distal end of a fiberoptic member which is heated with optical energy supplied to member 80 through an optical fiber (or wire in the case of a heated wire) running out through the introducer 10 to an optical source outside the patient's body, generally indicated as member 82.

What is claimed is:

1. Apparatus comprising:
    a biocompatible cylindrical introducer member with an outer wall and a hollow core, the cylindrical member having a longitudinal axis and an opening along a side extending in the direction of the longitudinal axis; and
    a rod with a U-shaped end that supports a cutting wire arranged perpendicular to the rod and positioned in the introducer member for cutting tissue entering the opening as the cutting wire travels with respect to the opening.

2. Apparatus of claim 1 wherein the U-shaped end bends away from the longitudinal axis.

3. Apparatus of claim 2 wherein the rod comprises a non-conductive material.

\* \* \* \* \*